(12) United States Patent
Ouchi et al.

(10) Patent No.: US 9,107,637 B2
(45) Date of Patent: Aug. 18, 2015

(54) X-RAY IMAGING APPARATUS AND WAVEFRONT MEASURING APPARATUS

(75) Inventors: Chidane Ouchi, Utsunomiya (JP); Naoki Kohara, Utsunomiya (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 710 days.

(21) Appl. No.: 13/511,896

(22) PCT Filed: Jan. 21, 2011

(86) PCT No.: PCT/JP2011/051680
§ 371 (c)(1),
(2), (4) Date: May 24, 2012

(87) PCT Pub. No.: WO2011/093417
PCT Pub. Date: Aug. 4, 2011

(65) Prior Publication Data
US 2012/0281217 A1    Nov. 8, 2012

(30) Foreign Application Priority Data

Jan. 28, 2010 (JP) ................................. 2010-016606

(51) Int. Cl.
*A61B 6/00* (2006.01)
*A61B 6/06* (2006.01)
(Continued)

(52) U.S. Cl.
CPC . *A61B 6/484* (2013.01); *A61B 6/06* (2013.01); *A61B 6/4291* (2013.01); *G21K 1/06* (2013.01); *A61B 6/027* (2013.01); *G21K 2207/005* (2013.01)

(58) Field of Classification Search
CPC ..... A61B 6/484; G21K 1/06; G21K 2207/005

USPC ................................................ 378/36, 62, 82
See application file for complete search history.

(56) References Cited

U.S. PATENT DOCUMENTS 7,180,979 B2    2/2007  Momose ......................... 378/62
7,440,115 B2   10/2008  Horwitz ........................ 356/512
(Continued)

FOREIGN PATENT DOCUMENTS

| EP | 1731099 | 12/2006 |
|----|---------|---------|
| JP | 2003-319928 | 11/2003 |
| JP | 4323955 | 9/2009 |

OTHER PUBLICATIONS

Zanette et al., "2D grating simulation for X-ray phase-contrast and dark-field imaging with a Talbot interferometer", Sep. 18, 2009, Proceedings of the 20th annual Congress on X-ray Optics and Microanalysis, CP1221, pp. 73-79.*

Creath, "Phase-measurement interferometry techniques", 1988, Progress in Optics XXVI, pp. 350-398.*

(Continued)

*Primary Examiner* — Allen C. Ho
*Assistant Examiner* — John Corbett
(74) *Attorney, Agent, or Firm* — Fitzpatrick, Cella, Harper & Scinto

(57) ABSTRACT

There is provided an X-ray imaging apparatus which images a specimen. The X-ray imaging apparatus comprises: an X-ray source; a diffraction grating configured to diffract an X-ray from the X-ray source; an X-ray detector configured to detect the X-ray diffracted by the diffraction grating; and a calculator configured to calculate phase information of the specimen on the basis of an intensity distribution of the X-ray detected by the X-ray detector, wherein the calculator obtains a spatial frequency spectrum from the plural intensity distributions, and calculates the phase information from the obtained spatial frequency spectrum.

14 Claims, 13 Drawing Sheets

(51) Int. Cl.
*G21K 1/06* (2006.01)
*A61B 6/02* (2006.01)

(56) References Cited

U.S. PATENT DOCUMENTS

| | | | |
|---|---|---|---|
| 8,009,797 B2* | 8/2011 | Ouchi et al. | 378/36 |
| 2003/0202688 A1 | 10/2003 | Sakaida | 382/128 |
| 2009/0110144 A1 | 4/2009 | Takahashi et al. | 378/62 |
| 2012/0236988 A1 | 9/2012 | Den et al. | 378/82 |
| 2012/0263274 A1 | 10/2012 | Ouchi | 378/62 |
| 2012/0281811 A1 | 11/2012 | Kohara et al. | 378/62 |

OTHER PUBLICATIONS

Momose et al., "High-speed x-ray phase imaging and x-ray phase tomography with Talbot interferometer and white synchrotron radiation", Jul. 9, 2009, Optics Express, vol. 17, No. 15, pp. 12540-12545.*

M. Takeda et al., "Fourier-Transform Method of Fringe-Pattern Analysis for Computer-Based Topography and Interferometry", *Journal of the Optical Society of America*, vol. 72, No. 1, pp. 156-160 (Jan. 1982).

JPO Office Action issued Jan. 28, 2014 in counterpart Japanese Patent Application No. 2010-016606, with translation.

* cited by examiner

CARRIER PEAKS

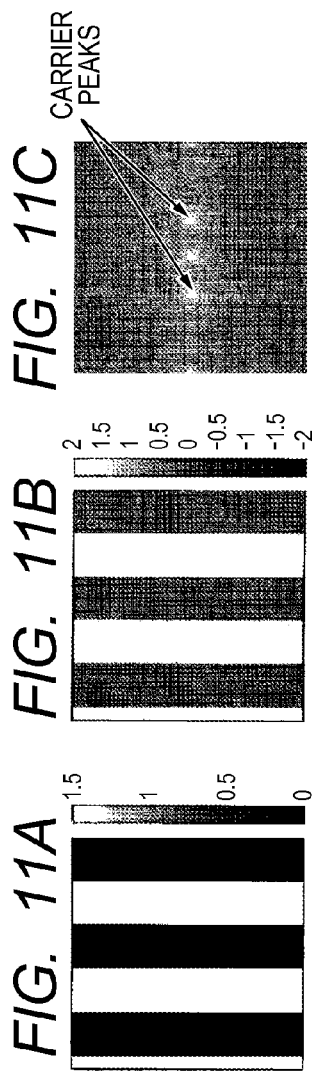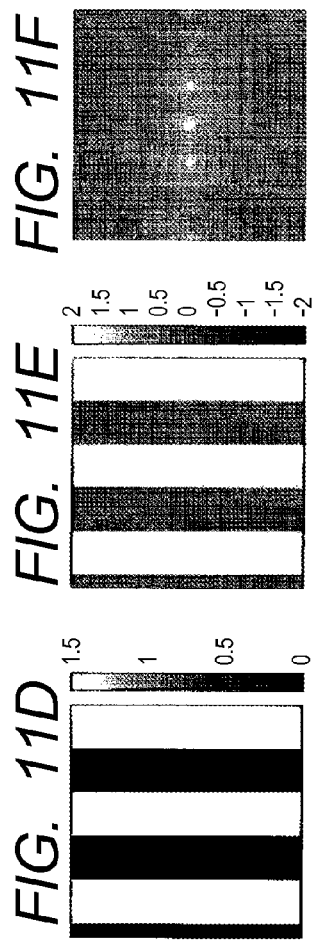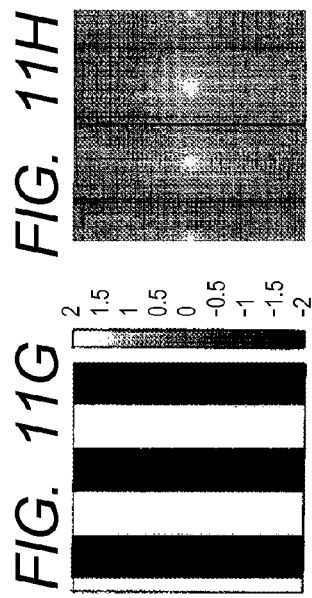

X-RAY IMAGING APPARATUS AND WAVEFRONT MEASURING APPARATUS

TECHNICAL FIELD

The present invention relates to an X-ray imaging apparatus which images a specimen, and a wavefront measuring apparatus which measures a transmitted wavefront of the specimen.

BACKGROUND ART

An X-ray has high transparency in various materials, and can achieve imaging with high spatial resolution. For these reasons, the X-ray is used for a nondestructive inspection of an object or a body as industrial utilization, X-raying as medical utilization, and the like.

That is, by the X-ray in the above utilization, a contrast image is formed by using a difference of absorption in a case where the X-ray transmits through an object or a living body, due to constituent elements and density differences of the object or the living body. It should be noted that such a process is called an X-ray absorption contrast method.

However, since an X-ray absorption capability of a light element is very small, it is difficult by the X-ray absorption contrast method to perform imaging of living soft tissue which consists of carbon, hydrogen, oxygen and the like being constituent elements of the living body, or a soft material.

On the other hand, in order to provide a method which can clearly perform imaging of even tissue consisting of light elements, a research for a phase contrast method using a phase difference of X-rays has been performed since 1990's.

Here, as one of various kinds of phase contrast methods, there is the method which is described in PTL 1.

The method described in PTL 1 is one kind of a method which is called a phase shift method. More specifically, in this method, an X-ray which was transmitted through a specimen is irradiated to a diffraction grating, and an intensity distribution (called as a self-image, hereinafter) which arises at a position away from the diffraction grating by a specific distance is imaged as a moiré fringe.

Then, phase information of an X-ray which transmitted through the specimen is obtained on the basis of three or more images which are obtained by scanning the moiré fringe as moving the diffraction grating. At this time, a differential wavefront in one direction is obtained. Therefore, in order to retrieve a wavefront shape, it is generally necessary to a differential wavefront in a direction perpendicular to the above direction.

Incidentally, a phase retrieval method which has been known as a Fourier transform method is disclosed in PTL 2. In this method, a Fourier transform is first performed to the self-image which consists of the fringe components in the mutually perpendicular directions arisen by using a two-dimensional diffraction grading, whereby a frequency map is obtained. Next, the peripheries of two peaks corresponding to the mutually perpendicular fringe components on the obtained frequency map are cut out, an inverse Fourier transform is performed to such respective cut-out regions, and the phases of the respective regions are calculated.

Incidentally, two phase distribution maps thus obtained respectively form differential wavefronts in the mutually perpendicular directions, and a wavefront retrieval process is performed based on these wavefronts, whereby two-dimensional wavefront retrieval is achieved from one interference image.

CITATION LISTS

Patent Literatures

PTL 1: U.S. Pat. No. 7,180,979
PTL 2: Japanese Pat. No. 4,323,955

Non Patent Literature

NPL 1: Mitsuo Takeda et al., J. Opt. Soc. Am., Vol. 72, Issue 1 (1982)

SUMMARY OF INVENTION

Technical Problem

In the method disclosed in PTL1, at least the three images are necessary to obtain the differential wavefront in one direction, and the differential wavefronts in the mutually perpendicular directions are necessary to retrieve the wavefront shape.

For these reasons, at least the six images are necessary in the imaging process, thereby increasing an X-ray radiation dose, and prolonging a measuring time. Thus, such matters become problems in case of applying the above-described method to a medical diagnostic apparatus.

On the other hand, a phase contrast image which is obtained in the method described in PTL 2 has a problem in a point that components which are caused by a transmissivity distribution of a specimen and uneven illumination of a light source are included in addition to a differential phase. For this reason, it is impossible to correctly measure a phase distribution which transmitted through the specimen.

In consideration of the above-described problems, the present invention aims to provide an X-ray imaging apparatus which measures an X-ray phase image of a specimen, in which the X-ray imaging apparatus enables to two-dimensionally retrieve a wavefront as suppressing an influence of a transmissivity distribution of the specimen and uneven illumination of a light source, by utilizing images the number of which is smaller than that in the method disclosed in PTL 1 and with spatial resolution which is higher than that in the method disclosed in PTL 2.

Solution to Problem

In one aspect of the present invention, an X-ray imaging apparatus, which images a specimen, comprises: an X-ray source; a diffraction grating configured to diffract an X-ray from the X-ray source; an X-ray detector configured to detect the X-ray diffracted by the diffraction grating; and a calculator configured to calculate phase information of the specimen on the basis of an intensity distribution of the X-ray detected by the X-ray detector, wherein the calculator obtains a spatial frequency spectrum from the plural intensity distributions, and calculates the phase information from the obtained spatial frequency spectrum.

Other aspects of the present invention will be clarified in the following exemplary embodiments of the present invention.

Advantageous Effects of Invention

According to the present invention, it is possible to achieve high-accurate X-ray phase image measurement which can eliminate a noise due to uneven illumination to a specimen and/or uneven transmission of the specimen and improve spatial resolution.

Further, it is possible to measure a transmitted wavefront on the conditions that the number of imaging operations is less than that in the phase shift method, spatial resolution is higher than that in the conventional Fourier transform method, and an error in the measured wavefront due to an uneven transmissivity of the specimen and uneven illumination of the light source is reduced.

Further features of the present invention will become apparent from the following description of exemplary embodiments with reference to the attached drawings.

BRIEF DESCRIPTION OF DRAWINGS

FIGS. 11A, 11B, 11C, 11D, 11E, 11F, 11G and 11H are diagrams for describing intensity distributions and frequency spectra in a case where a diffraction grating which has periodicity in one direction, in an example 4 of the present invention.

DESCRIPTION OF EMBODIMENTS

Hereinafter, exemplary embodiments of the present invention will be described.

First Embodiment

As a first embodiment, a constructive example of an X-ray imaging apparatus to which the present invention is applied will be described with reference to FIG. 1.

Figure 1:
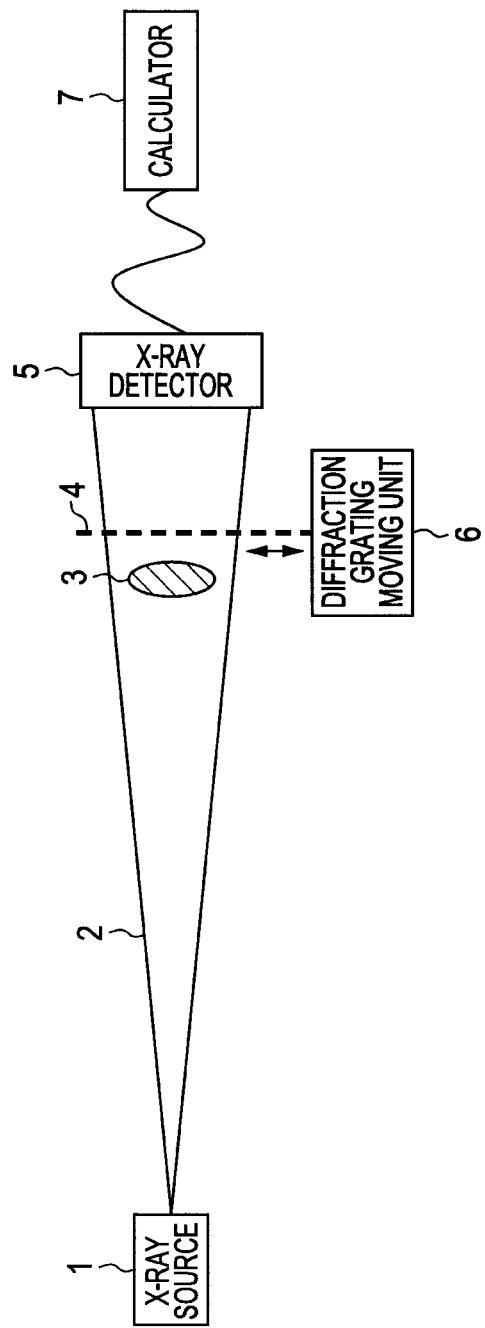
FIG. 1 is a block diagram for describing a constructive example of an X-ray imaging apparatus according to a first embodiment and an example 1 of the present invention.

FIG. 1 illustrates an X-ray source 1 which radiates an X-ray, an X-ray 2 which is radiated by the X-ray source 1, a specimen 3 which is to be imaged and measured by the X-ray imaging apparatus, and a diffraction grating 4 which periodically modifies a phase or intensity of an incident X-ray in two directions which are perpendicular to each other.

Further, FIG. 1 illustrates an X-ray detector 5 which detects an intensity distribution which arises by a Talbot effect based on the X-ray which transmitted through (or was reflected on) the diffraction grating, a diffraction grating moving unit 6 which changes an in-plane position of the diffraction grating 4, and a calculator 7 which calculates a differential wavefront and a transmitted wavefront from an image which has been imaged by the X-ray detector 5.

Namely, the X-ray imaging apparatus according to the present embodiment includes the X-ray source 1, the diffraction grating 4, the diffraction grating moving unit 6, the X-ray detector 5, and the calculator 7.

More specifically, the calculator 7 includes a spectrum calculation means which obtains a spatial frequency spectrum of a difference between two imaging intensity distributions obtained by using the diffraction grating moving unit 6 and the X-ray detector 5, a spectrum separation means which cuts out, from the spatial frequency spectrum obtained by the spectrum calculation means, a frequency component in a period of the imaging intensity distribution, and a differential phase calculation means which calculates a differential phase distribution by performing an inverse Fourier transform to the frequency component obtained by the spectrum separation means.

Hereinafter, the present embodiment will further be described in detail. In the above constitution, the diffraction grating 4 is disposed immediately before or immediately after the specimen 3 to function so that the X-ray which transmitted through the diffraction grating 4 forms the periodic intensity distribution on the X-ray detector 5.

More specifically, the diffraction grating 4 can be constituted by a phase modulation grating which consists of an X-ray transmission member of which the thickness periodically changes, an intensity modulation grating which has periodically arranged openings, or the like.

In order to obtain a clear intensity distribution, a distance $Z_1$ between the diffraction grating 4 and the X-ray detector 5 satisfies an expression (1) of Talbot condition as indicated below.

$$(1/Z_0)+(1/Z_1)=(1/N)\times(\lambda/d^2) \qquad (1)$$

In the above expression (1), $Z_0$ indicates a distance between the X-ray source 1 and the diffraction grating 4, $\lambda$ is a wavelength of the X-ray, and d indicates a grating period of the diffraction grating 4. Further, N is a real number which is expressed as $n/2-\frac{1}{4}$ (n is a natural number) in a case where a phase modulation grating which has checks respectively having a phase difference $\pi/2$ is used, a real number which is expressed as $n/4-\frac{1}{8}$ in a case where a phase modulation grating which has checks respectively having a phase difference $\pi$ is used, and a real number which is expressed as n in a case where an intensity modulation grating of a mesh pattern is used.

If an inclination of the wavefront changes according to the transmission of the X-ray through the specimen 3, the radiation direction of the X-ray changes. Thus, the intensity distribution on the X-ray detector moves.

Generally, it is possible to obtain an inclination of the transmitted wavefront (called the differential wavefront, hereinafter) on the specimen 3, by utilizing a Fourier transform method to an intensity distribution image obtained by the X-ray detector. Here, since the detail of the Fourier transform method is described in NPL 1, only an outline thereof will be described here.

That is, in a frequency spectrum which is obtained by performing a two-dimensional Fourier transform to an intensity distribution, there arise peaks which correspond to a frequency (called a carrier frequency, hereinafter) of a fundamental period component of the intensity distribution (called a carrier fringe, hereinafter) and numerous its harmonic components. Then, the periphery of one of the two peaks which respectively correspond to the perpendicular carrier frequencies is cut out, and such a cut-out component is moved to the center. Further, an inverse Fourier transform is performed to the moved component, and a phase component thereof is obtained, whereby it is possible to obtain a differential wavefront in one direction of a wavefront to be measured.

To retrieve the wavefront, it is necessary to integrate the obtained differential wavefront in a differential direction. However, in general, a change of a wavefront in the direction perpendicular to the differential direction cannot be calculated only by such a process. Namely, it is possible to solve such a problem by performing the same process as described above to the other of the two peaks and thus obtaining the differential wavefronts in the perpendicular two directions.

In the present embodiment, the diffraction grating 4 is moved within a plane by the diffraction grating moving unit 6, whereby the frequency spectrum of a difference between the two images which are imaged as moving a carrier fringe of the intensity distribution by a half period.

Incidentally, how to obtain the frequency spectrum of the difference between the relevant two images will be briefly described hereinafter. Namely, a subtraction between the two images is first performed, and the Fourier transform may be performed to such an obtained difference image. Alternatively, the Fourier transform is first performed to the two images to calculate the frequency spectra of the respective images, and then a subtraction may be performed between the calculated frequency spectra.

Particularly, in the present embodiment, since the diffraction grating is moved within the plane, the intensity distribution is moved by half of its period. Here, the intensity distribution is imaged before and after the movement. Then, the difference between the two images thus obtained is calculated by the calculator, and the Fourier transform method is applied to the calculated difference image, whereby the inclination of the transmitted wavefront on the specimen is obtained.

Since uneven illumination to the specimen or uneven transmission of the specimen produces the same pattern respectively in the two images, it is possible to eliminate an influence of the uneven illumination and/or the uneven transmission by obtaining the difference between these images. Further, it is also possible to eliminate a peak of a second harmonic of a carrier which restricts spatial resolution in the wavefront measurement by the Fourier transform method, thereby improving the spatial resolution.

As described above, according to the present embodiment, it is possible to achieve high-accurate X-ray phase image measurement which can eliminate a noise due to the uneven illumination to the specimen and/or the uneven transmission of the specimen and improve the spatial resolution.

Second Embodiment

Subsequently, as a second embodiment, a wavefront measuring apparatus to which the first embodiment is applied will be described.

In the present embodiment, the constitution of the first embodiment is applied to the wavefront measuring apparatus which inspects a shape and an internal property of an optical element on the basis of a measured result of a transmitted wavefront.

Namely, the wavefront measuring apparatus according to the present embodiment includes a light source, a diffraction grating which periodically modifies a phase or an intensity of the a light ray irradiated from the light source, and a moving unit which changes an in-plane position of the diffraction grating. Further, the wavefront measuring apparatus includes an imaging device which obtains an intensity distribution which arises by a Talbot effect due to the light ray transmitting through or reflected on the diffraction grating, or an intensity distribution of a moiré fringe which arises by further disposing a shielding member. Furthermore, the wavefront measuring apparatus is constituted to have a calculator which obtains a differential phase distribution of the light ray transmitting through the specimen disposed between the light source and the diffraction grating or between the diffraction grating and the imaging device, and thus measure the transmitted wavefront of the specimen. Here, it should be noted that the moving unit can be provided by the diffraction grating moving unit in the first embodiment and the calculator can be provided by the calculator in the first embodiment.

As described above, according to the present embodiment, it is possible to measure the transmitted wavefront on the conditions that the number of imaging operations is less than that in the phase shift method, the spatial resolution is higher than that in the conventional Fourier transform method, and an error in the measured wavefront due to an uneven transmissivity of the specimen and uneven illumination of the light source is reduced.

EXAMPLES

Hereinafter, examples of the present invention will be described.

Example 1

As an example 1, a constructive example of the X-ray imaging apparatus will be described with reference to FIG. 1.

In the X-ray imaging apparatus of this example, the X-ray 2 radiated by the X-ray source 1 reaches the X-ray detector 5 through the specimen 3 and the diffraction grating 4.

Here, the diffraction grating 4 is the phase modulation grating which modulates the phase of the incident X-ray by $\pi/2$ or $\pi$ or the intensity modulation grating which modulates the intensity of the incident X-ray.

If the phase modulation grating is used, the relevant phase modulation grating is made by silicon of which the X-ray transmissivity is large and which is well workable. On the other hand, if the intensity modulation grating is used, the relevant intensity modulation grating is made by gold of which the X-ray transmissivity is small.

Initially, a case where the phase modulation grating of the phase difference $\pi/2$ is used as the diffraction grating will be described.

Namely, the phase modulation grating of the phase difference $\pi/2$ in which the portions that the phases of the transmission X-ray are relatively different from others by $\pi/2$ are two-dimensionally and periodically arranged by periodically changing the thickness of the silicon is formed.

Figure 2:
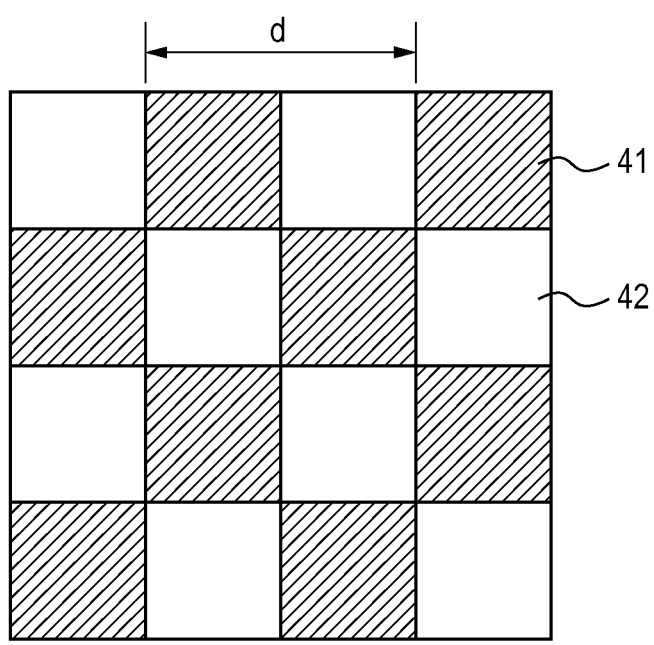
FIG. 2 is a diagram for describing a checked phase grating of the X-ray imaging apparatus according to the example 1 of the present invention.

FIG. 2 is a diagram which is obtained by viewing one portion of the diffraction grating in this example from the side of the light source.

That is, the thickness of the diffraction grating is made to have differences so that a transmission phase of a portion 41 having hatched lines is different from a transmission phase of a portion 42 not having hatched lines by $\pi/2$. Further, these portions are two-dimensionally arranged with a period d.

Figure 3:
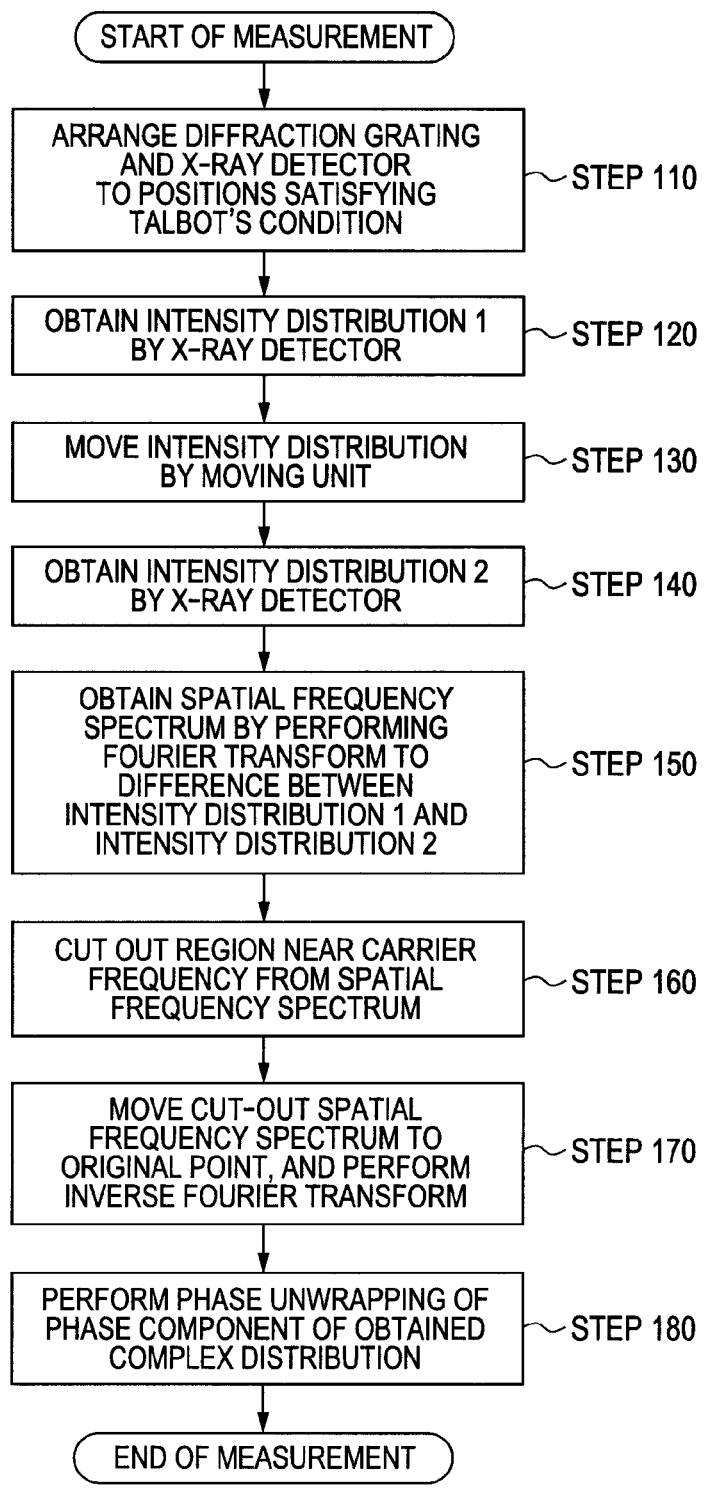
FIG. 3 is a flow chart indicating a wavefront measuring process to be performed by a calculator according to the example 1 of the present invention.

FIG. 3 is a flow chart indicating a wavefront measuring process to be performed in this example.

In a step 110, the X-ray detector is arranged so that the distance $Z_1$ between the diffraction grating and the X-ray detector satisfies the expression (1) in case of N=¼, whereby a clear intensity distribution image arises on the X-ray detector.

In a step 120, the intensity distribution is obtained by the X-ray detector, and the obtained intensity distribution is set as an intensity distribution 1.

Figure 4:
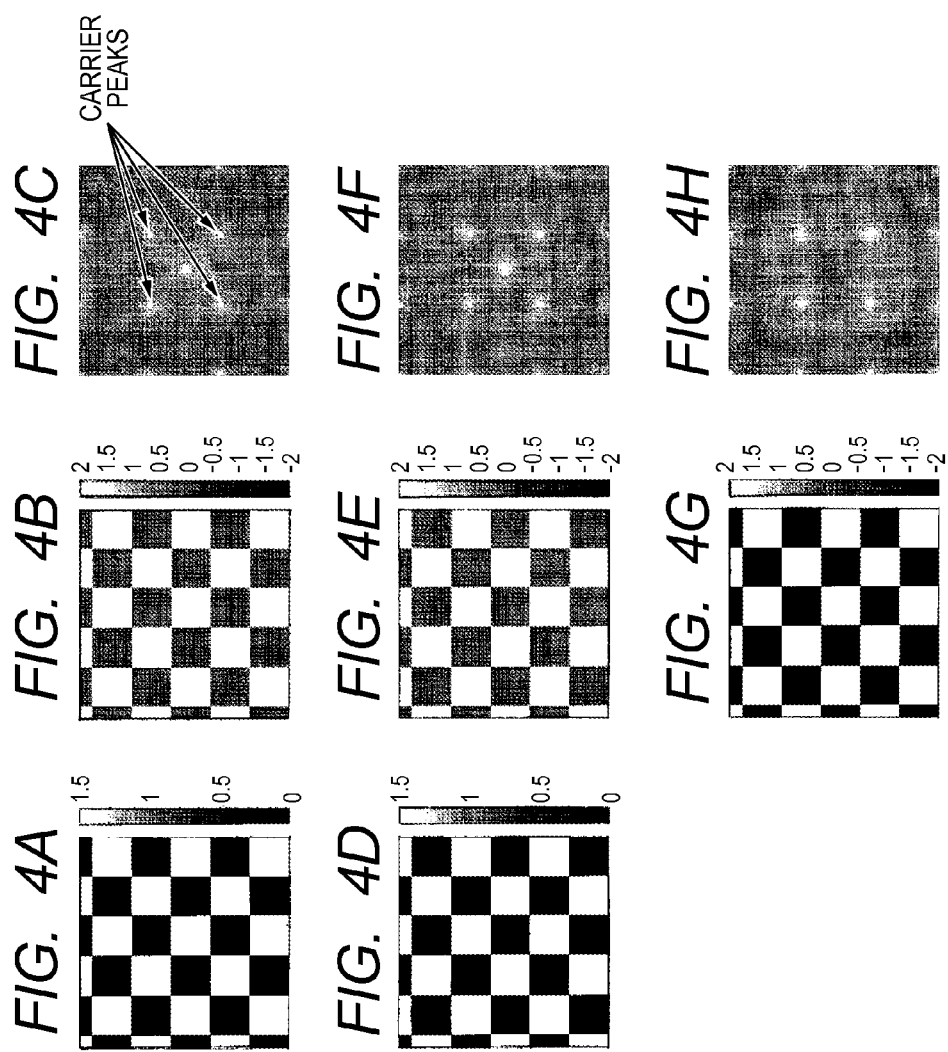
FIGS. 4A, 4B, 4C, 4D, 4E, 4F, 4G and 4H are diagrams for describing intensity distributions and frequency spectra in a case where a phase modulation grating which has checks respectively having a phase difference $\pi/2$ is used, in the example 1 of the present invention.

FIGS. 4A, 4B and 4C respectively illustrate the position state of the diffraction grating 4 at this time, the intensity distribution on the X-ray detector, and the frequency spectrum obtained by performing the two-dimensional Fourier transform to the intensity distribution on the X-ray detector.

In a step 130, the intensity distribution is moved by ½ of the period by moving, with the diffraction grating moving unit 6, the diffraction grating 4 in the vertical or horizontal direction by a half period, i.e., ½ of the period d illustrated in FIG. 2.

In a step 140, the intensity distribution is again obtained by the X-ray detector, and the obtained intensity distribution is set as an intensity distribution 2.

FIGS. 4D, 4E and 4F respectively illustrate the position state of the diffraction grating 4 at this time, the intensity distribution on the X-ray detector, and the frequency spectrum obtained by performing the two-dimensional Fourier transform to the intensity distribution on the X-ray detector.

Here, it should be noted that FIGS. 4C and 4F seem the same because light and shade are represented on the drawing sheet according to the magnitudes of the absolute values of the frequency spectra. Namely, a sign of the carrier peak being the peak corresponding to the carrier fringe in FIG. 4C is reversed in regard to that in FIG. 4F.

On the other hand, since the peak at the center of the frequency spectrum corresponds to the component which arises from uneven illumination to the specimen and uneven transmission of the specimen but does not arise from movement of the carrier, a sign of the peak is unchanged. For this reason, it is possible to eliminate the peak at the center by obtaining a difference between the intensity distribution 1 and the intensity distribution 2. In a step 150, the frequency spectrum of the difference between the intensity distributions before and after the movement of the diffraction grating is obtained.

FIG. 4G illustrates the difference between the intensity distributions before and after the movement of the diffraction grating.

FIG. 4H illustrates the frequency spectrum of the difference between these intensity distributions. Here, it can be understood that the peak at the center has disappeared.

Incidentally, it is needless to say that, in case of calculating the frequency spectrum of the difference between the intensity distributions before and after the movement of the diffraction grating, it is possible to first calculate the frequency spectra of the intensity distributions 1 and 2 and then calculate the difference between the calculated frequency spectra.

In a step 160, a region near the carrier frequency is cut out. Here, if the region to be cut out (called the cut-out region) is made large, spatial resolution of the differential phase distribution to be calculated in a later step improves.

However, in order to reduce an influence of peak other than the carrier peak, the cut-out region is restricted to be within the intermediate line between the carrier peak and the peak other than the carrier peak.

Figure 5:
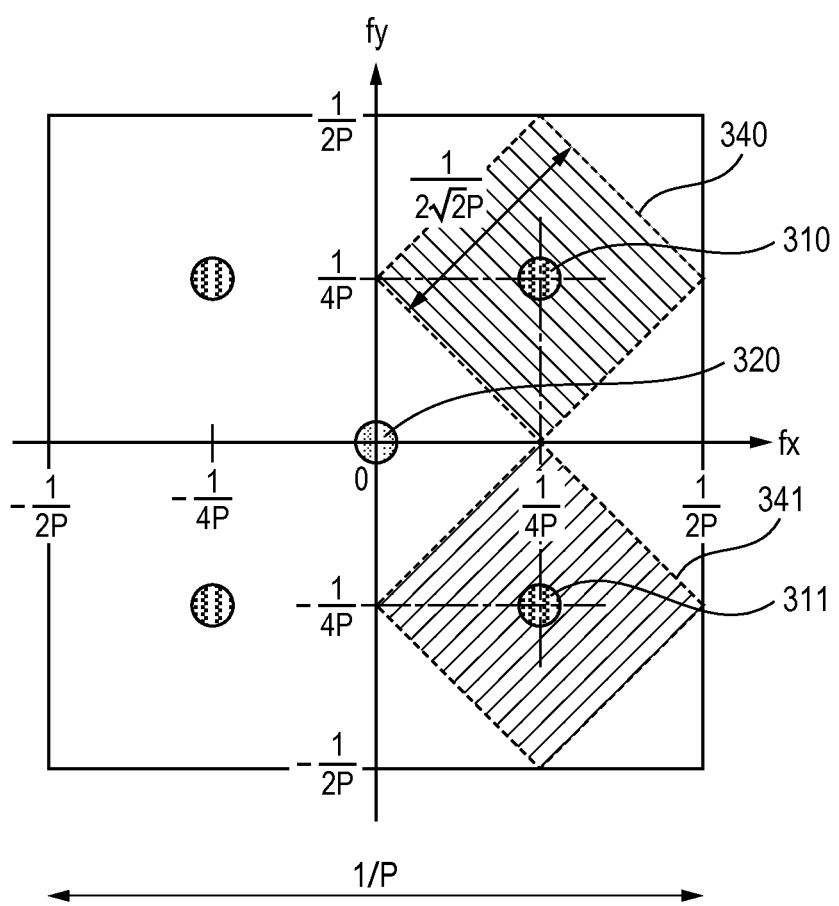
FIG. 5 is a diagram for describing a frequency spectrum cut-out region in a case where the present invention is not applied.

FIG. 5 is a diagram for describing the cut-out region in a case where the present invention is not applied, that is, in a case where the difference between the intensity distributions is not obtained. As illustrated in the drawing, cut-out regions 340 and 341 are a maximum region as the cut-out regions in the two directions perpendicular to each other as centering on the carrier frequency.

If it is assumed that a pixel size of the X-ray detector is P, an absolute value of a spatial frequency capable of being expressed (called an expressible spatial frequency) is restricted to be equal to or lower than a Nyquist frequency, i.e., within a range of ±1/2P. Further, the expressible spatial frequencies are restricted inside the intermediate line between carrier peaks 310 and a peak 320 at the center and inside intermediate line between carrier peaks 311 and a peak 320. For this reason, the maximum cut-out region is inside the two squares which have the peaks 310 and 311 as the respective centers, of which each side is ½√2P, and which incline by 45°.

Figure 6:
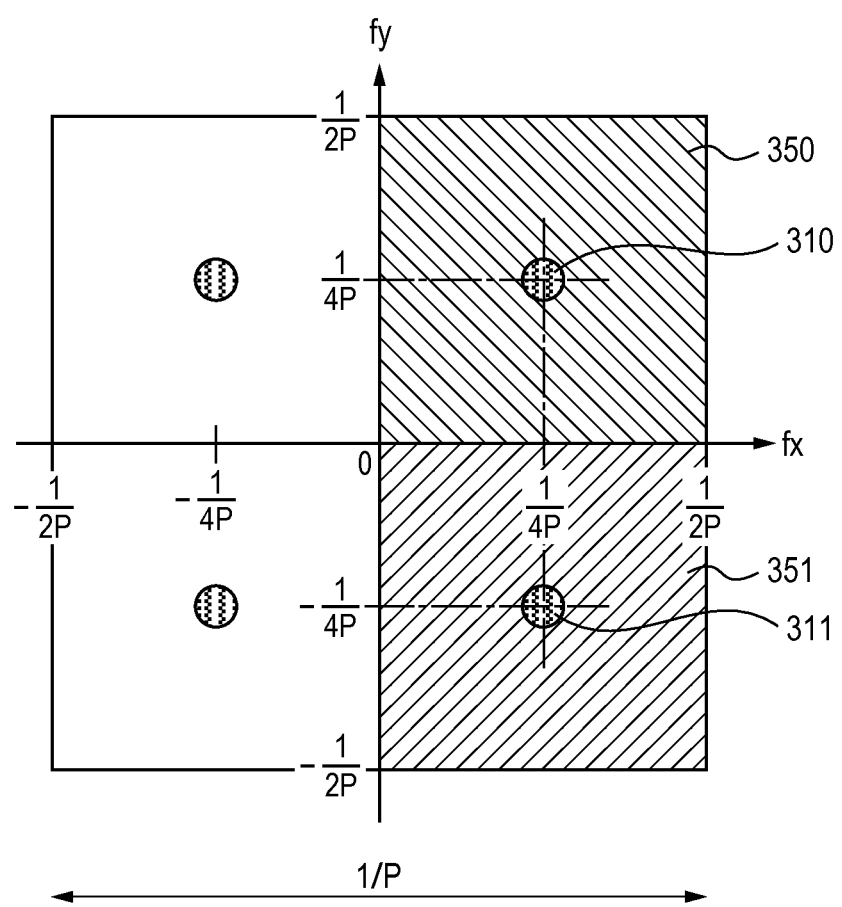
FIG. 6 is a diagram for describing a frequency spectrum cut-out region in the example 1 of the present invention.

On the other hand, FIG. 6 is a diagram for describing the cut-out region in a case where the present invention is applied. As illustrated in the drawing, cut-out regions 350 and 351 are a maximum region as the cut-out regions in the two directions perpendicular to each other as centering on the carrier frequency.

Since the peak at the center has disappeared, the cut-out region can be increased up to the intermediate line between the adjacent carrier peaks.

Therefore, the maximum cut-out region is inside the erected two squares which have the peaks 310 and 311 as the respective centers, and of which each side is ±1/2P.

Since the area of the cut-out regions 350 and 351 in FIG. 6 is twice the area of the cut-out regions 340 and 341 in FIG. 5, the frequency components which can be retrieved in FIG. 6 are large accordingly, whereby it is possible to resultingly obtain an X-ray phase image of which the spatial resolution is high.

In a step 170, the spatial frequency spectrum which has been cut out is moved to the original point, and an inverse Fourier transform is performed.

In a step 180, a phase component of a complex distribution obtained in the step 170 is calculated. Since the calculated phase has been generally convoluted into 0 to $2\pi$, the differential phase distribution is obtained by performing phase unwrapping. Further, if the differential phase is integrated so that the obtained differential phases in the two directions perpendicular to each other are simultaneously satisfied, the phase distribution of the X-ray which transmitted through the specimen, i.e., the transmitted wavefront, can be obtained as need arises.

Incidentally, as another method of obtaining the phase distribution, there may be a method of fitting the differential phase to a differential function sequence which is obtained by differentiating a function sequence such as a Zernike polynomial or the like to a periodicity direction of the carrier fringe. Further, if the sum of the intensity distributions 1 and 2 is obtained as need arises, information indicating X-ray transmission of the specimen can be obtained because the carrier peak disappears.

Subsequently, a case where the phase modulation grating of the phase difference π is used as the diffraction grating will be described. However, the process which is the same as that to be performed in the above-described case where the phase modulation grating of the phase difference π/2 is used will be omitted.

In the step 130, the diffraction grating is moved so that the intensity distribution on the X-ray detector is deviated in both the vertical and horizontal directions by a half period. The distance by which the diffraction grating is moved is $1/\sqrt{2}$ of the case where the phase modulation grating of the phase difference π/2 is used, and the direction in which the diffraction grating is moved is the direction which inclines by 45° from the case where the phase modulation grating of the phase difference π/2 is used.

Figure 7:
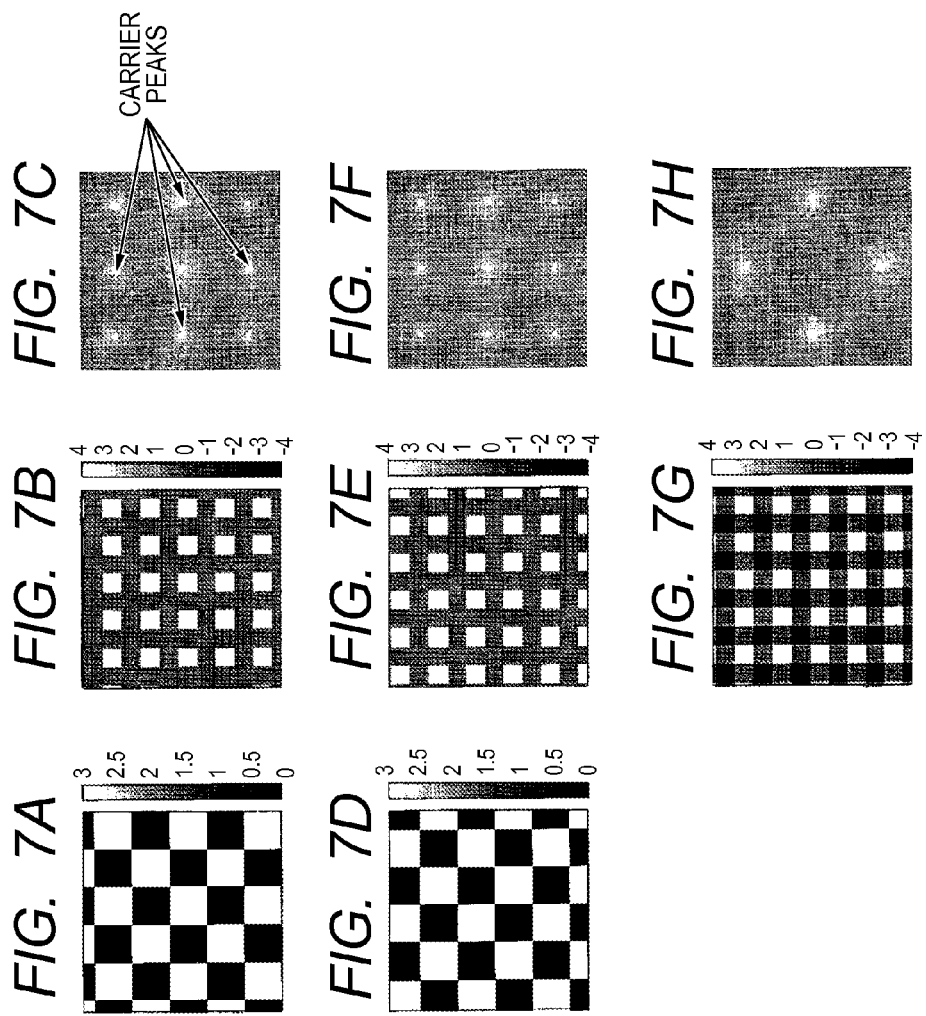
FIGS. 7A, 7B, 7C, 7D, 7E, 7F, 7G and 7H are diagrams for describing intensity distributions and frequency spectra in a case where a phase modulation grating which has checks respectively having a phase difference $\pi$ is used, in the example 1 of the present invention.

FIGS. 7A, 7B and 7C respectively illustrate the position state of the diffraction grating, the intensity distribution on the X-ray detector, and the frequency spectrum obtained by performing the two-dimensional Fourier transform to the intensity distribution on the X-ray detector, in the case where the phase modulation grating of the phase difference π is used.

FIGS. 7D, 7E and 7F respectively illustrate the position state of the diffraction grating, the intensity distribution on the X-ray detector, and the frequency spectrum obtained by performing the two-dimensional Fourier transform to the intensity distribution on the X-ray detector, after the diffraction grating was moved.

FIG. 7G illustrates the difference between the intensity distributions before and after the movement of the diffraction grating, and FIG. 7H illustrates the difference between the frequency spectra before and after the movement of the diffraction grating.

As well as the case where the phase modulation grating of the phase difference π/2 is used, since unnecessary peaks other than the carrier peak disappear, a difference in the calculated differential phase distribution is recued.

Moreover, since the unnecessary peaks disappear, it is possible to make the cut-out region of the frequency spectrum in the step 160 large, whereby it is possible to resultingly obtain the X-ray phase image of which the spatial resolution is high.

Further, a case where an intensity modulation grating having a mesh pattern is used as the diffraction grating will be described. However, the process which is the same as that to be performed in the above-described case where the phase modulation grating of the phase difference π/2 is used will be omitted.

In the step 130, the diffraction grating is moved so that the intensity distribution on the X-ray detector is deviated in both the vertical and horizontal directions by a half period. Namely, if it is assumed that the period of the diffraction grating is d as illustrated in FIG. 8A, the diffraction grating is moved in both the vertical and horizontal directions by d/2.

Figure 8:
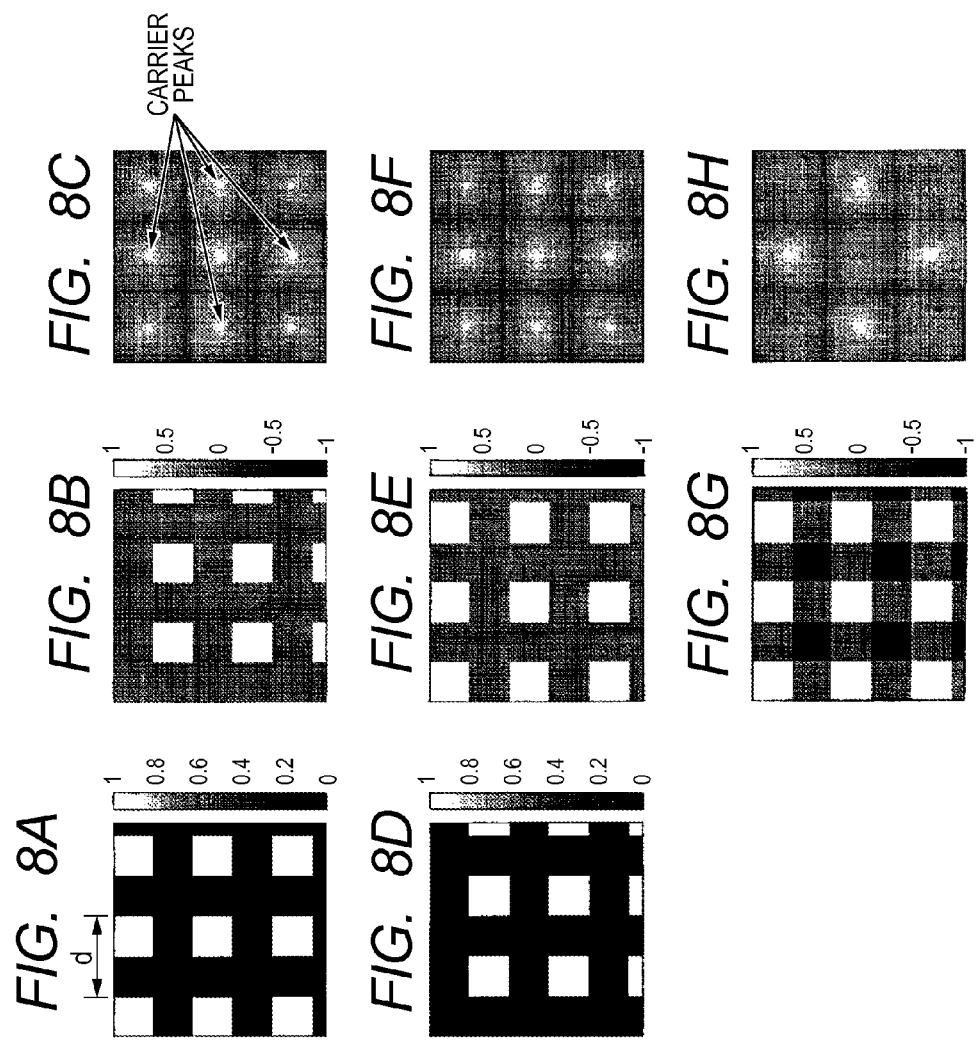
FIGS. 8A, 8B, 8C, 8D, 8E, 8F, 8G and 8H are diagrams for describing intensity distributions and frequency spectra in a case where an intensity modulation grating of a mesh pattern is used, in the example 1 of the present invention.

FIGS. 8A, 8B and 8C respectively illustrate the position state of the diffraction grating, the intensity distribution on the X-ray detector, and the frequency spectrum obtained by performing the two-dimensional Fourier transform to the intensity distribution on the X-ray detector, in a case where the intensity modulation grating which includes transmission portions and shielding (or light shielding) portions is used.

FIGS. 8D, 8E and 8F respectively illustrate the position state of the diffraction grating, the intensity distribution on the X-ray detector, and the frequency spectrum obtained by performing the two-dimensional Fourier transform to the intensity distribution on the X-ray detector, after the diffraction grating was moved. Incidentally, in FIGS. 8A and 8D, the black portions indicate the shielding portions respectively.

FIG. 8G illustrates the difference between the intensity distributions before and after the movement of the diffraction grating, and FIG. 8H illustrates the difference between the frequency spectra before and after the movement of the diffraction grating. As well as the case where the phase modulation grating of the phase difference π/2 is used, since unnecessary peaks other than the carrier peak disappear, a difference in the calculated differential phase distribution is recued.

Moreover, since the unnecessary peaks disappear, it is possible, as well as the case where the phase modulation grating of the phase difference π/2 is used, to make the cut-out region of the frequency spectrum in the step 160 large, whereby it is possible to resultingly obtain the X-ray phase image of which the spatial resolution is high.

Example 2

Figure 9:
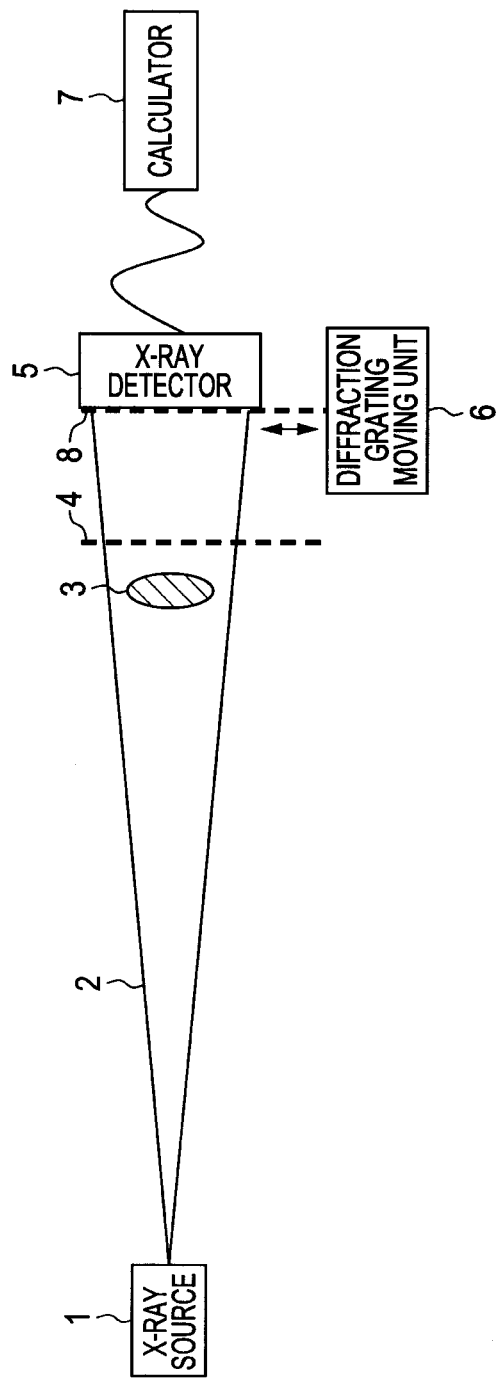
FIG. 9 is a block diagram for describing a constructive example of an X-ray imaging apparatus according to an example 2 of the present invention.

As an example 2, a constructive example of the X-ray imaging apparatus which is different from that in the example 1 will be described with reference to FIG. 9.

In this example, only portions which are different from the example 1 will be described.

It should be noted that this example is effective to reduce a size of the X-ray imaging apparatus in which a Talbot interference is used.

Here, to reduce the size of the X-ray imaging apparatus, it is necessary to reduce the period d of the diffraction grating so that the distances $Z_0$ and $Z_1$ in the expression (1) become small. Therefore, since the period of the intensity distribution is approximately equal to or less than the existing pixel of the X-ray detector, it is impossible to retrieve the wavefront by the Fourier transform method. Consequently, a moiré fringe is formed by a shielding member which has a period slightly different from the period of the intensity distribution by the Talbot interference, and the wavefront is retrieved based on a distortion of the intensity distribution enlarged to the moiré fringe.

In this example, a shielding member 8 which has a period slightly different from the period of the intensity distribution is disposed immediately before the X-ray detector 5, thereby forming the moiré fringe and thus obtaining the intensity distribution of the moiré fringe.

More specifically, since the distortion has arisen in the moiré fringe based on the phase distribution of the X-ray which transmitted through the specimen 3, the differential phase distribution or the phase distribution of the X-ray which transmitted through the specimen 3 is obtained according to the procedure of FIG. 3 same as that in the example 1.

Unlike the example 1, second imaging corresponding to the step 130 is performed as moving the period of the moiré fringe by a half period.

Here, to move the distribution of the moiré fringe on the X-ray detector, it may move the diffraction grating 4 within the plane of the diffraction grating.

Otherwise, it may move the shielding member 8 within the plane of the making member.

According to the steps 140 to 180, even if the size of the apparatus is small, it is possible to measure the wavefront on which an error in the measured wavefront due to an uneven transmissivity of the specimen and uneven illumination of the light source has been reduced. Further, if it is designed that the region to be cut out from the spatial frequency spectrum becomes maximum as illustrated in FIG. 6, the spatial resolution of the calculated differential phase distribution or the calculated phase distribution is maximized.

Example 3

As an example 3, a constructive example of the X-ray imaging apparatus which is different from those in the examples 1 and 2 will be described with reference to FIGS. 10A to 10N.

In this example, only portions which are different from the examples 1 and 2 will be described.

In this example, with respect to the checked phase modulation grating which has the phase difference π and is used as the diffraction grating, even if the phase difference is deviated from π due to a defect in manufacturing or the checks are deformed, it enables to eliminate a noise due to uneven illumination to the specimen and/or uneven transmission of the specimen, and it enables to measure the transmitted wavefront of the specimen with a high degree of accuracy on the condition that the spatial resolution has been improved.

If the phase difference of the phase modulation grating having the phase difference π is deviated from π due to the defect in manufacturing and/or if the checks in the periodic structure are deviated from rectangles, zero-dimensional light which does not exist ideally is generated. Then, if the zero-dimensional light is generated, an interference between the zero-dimensional light and plus and minus one-dimensional light arises. Thus, an intensity distribution of a lower frequency is generated, whereby an error arises in the phase calculation by the Fourier transform method.

Figure 10A:
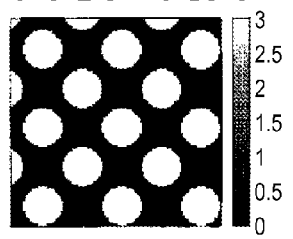
FIGS. 10A, 10B, 10C, 10D, 10E, 10F, 10G, 10H, 10I, 10J, 10K, 10L, 10M and 10N are diagrams for describing intensity distributions and frequency spectra in a case where a phase modulation grating which has a manufacturing error and has checks respectively having a phase difference $\pi$ is used, in an example 3 of the present invention.
Figure 10B:
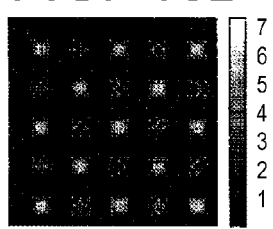
Figure 10C:
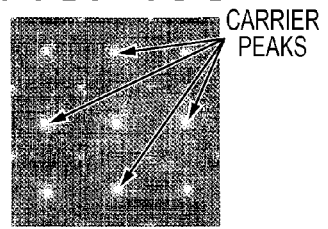

FIGS. 10A, 10B and 10C respectively illustrate the position state of the diffraction grating, the intensity distribution on the X-ray detector, and the frequency spectrum obtained by performing the two-dimensional Fourier transform to the intensity distribution on the X-ray detector, in a case where the phase modulation grating of the phase difference π in which the periodic structure thereof has been deviated from the checks due to the defect in manufacturing is used.

Here, it can be understood that, in the frequency spectrum of FIG. 10C, a frequency spectrum which does not exist in the frequency spectrum of FIG. 7C in the case where a defect in manufacturing does not arises exists.

The spectrum which arises due to the defect in manufacturing of the diffraction grating cannot be eliminated by the difference spectrum of which the obtaining procedure is indicated in FIG. 3. Thus, in this example, a differential phase distribution is calculated based on four imaging intensity distributions obtained by moving the intensity distribution on the X-ray detector.

As well as FIGS. 7D, 7E and 7F, FIGS. 10D, 10E and 10F respectively illustrate the position state of the diffraction grating, the intensity distribution on the X-ray detector, and the frequency spectrum obtained by performing the two-dimensional Fourier transform to the intensity distribution on the X-ray detector, in a case where the diffraction grating is moved.

Incidentally, the diffraction grating is moved so that the intensity distribution on the X-ray detector is deviated in the periodic vertical and horizontal directions by a half period.

Figure 10D:
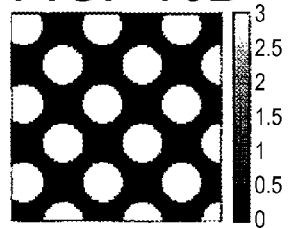
Figure 10E:
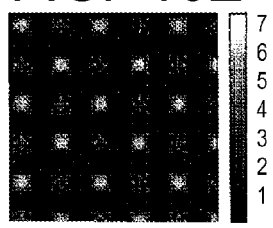
Figure 10F:
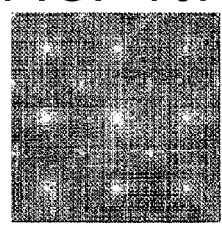
Figure 10G:
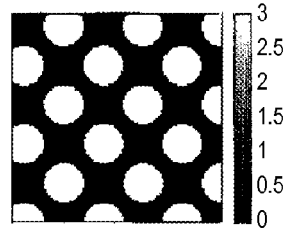
Figure 10H:
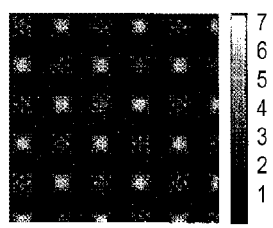
Figure 10I:
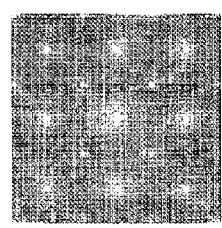

FIGS. 10G, 10H and 10I respectively illustrate the position state of the diffraction grating, the intensity distribution on the X-ray detector, and the frequency spectrum obtained by performing the two-dimensional Fourier transform to the intensity distribution on the X-ray detector, in a case where the diffraction grating is moved by the movement amount same as that in the movement of the diffraction grating indicated in FIG. 10D and in the direction perpendicularly changed by 90° from that in the movement of the diffraction grating indicated in FIG. 10D.

Figure 10J:
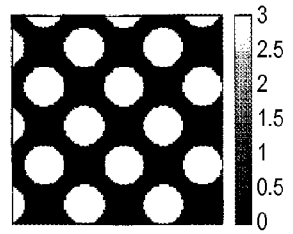
Figure 10K:
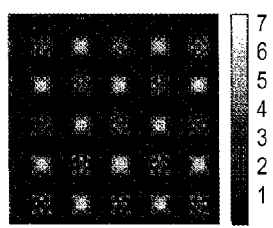
Figure 10L:
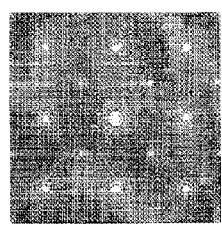

FIGS. 10J, 10K and 10L respectively illustrate the position state of the diffraction grating, the intensity distribution on the X-ray detector, and the frequency spectrum obtained by performing the two-dimensional Fourier transform to the intensity distribution on the X-ray detector, in a case where both the movement of the diffraction grating indicated in FIG. 10D and the movement of the diffraction grating indicated in FIG. 10G are performed.

Figure 10M:
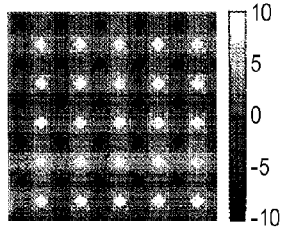

Here, if it is assumed that the imaging intensity distribution corresponding to FIG. 10B is IA, the imaging intensity distribution corresponding to FIG. 10E is IB, the imaging intensity distribution corresponding to FIG. 10H is IC, and the imaging intensity distribution corresponding to FIG. 10K is ID, then the intensity distribution corresponding to IA−IB−IC+ID is indicated in FIG. 10M.

In this regard, the imaging intensity distributions respectively indicated by IA to ID are the imaging intensity distributions which are obtained as indicated below.

That is, a moving unit is constituted by a first moving unit which can change the in-plane position of the diffraction grating so as to move the period of the intensity distribution in both the perpendicular two periodicity directions by ½, and a second moving unit which changes the position of the diffraction grating or the shielding member in the same plane as that of the first moving unit, in the direction perpendicular to that of the first moving unit, and by the same distance as that of the first moving unit.

Then, the imaging intensity distribution IA is obtained without using the moving unit, and the imaging intensity distribution IB is obtained by using only the first moving unit. Further, the imaging intensity distribution IC is obtained by using only the second moving unit, and the imaging intensity distribution ID is obtained by using the first moving unit and the second moving unit.

Figure 10N:
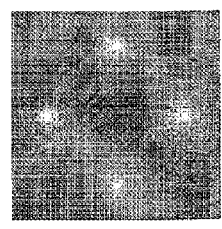

FIG. 10N indicates the frequency spectrum which is obtained by performing the two-dimensional Fourier transform to the intensity distribution indicated in FIG. 10M. It can be understood from this drawing that the spectrum which arose due to the defect in manufacturing of the diffraction grating has been eliminated.

In this example, as described above, with respect to the intensity distribution which is obtained by the expression (IA−IB−IC+ID) in which the imaging intensity distributions respectively obtained at the four diffraction grating positions are added/subtracted, the differential phase distribution or the phase distribution is calculated on the basis of the frequency spectrum obtained by the two-dimensional Fourier transform.

Here, the calculation of the phase at this time is performed according to the steps 160, 170 and 180 respectively described in the example 1.

According to this example, since the spectrum which arises due to the defect in manufacturing of the diffraction grating is eliminated, it is possible to increase accuracy of the phase calculation in the Fourier transform method.

In the above-described examples 1 to 3, the diffraction grating, the shielding member or the X-ray detector is disposed so that the period of the intensity distribution or the intensity distribution of the moiré fringe has the size being 2√2 times the pixel size of the X-ray detector and the periodicity direction of the relevant intensity distribution inclines from the pixel arrangement of the X-ray detector by 45°. Further, the spectrum separation means in the calculator is constructed to be able to cut out, from the spatial frequency spectrum obtained by the Fourier transform, the rectangular region which includes the frequencies from the zero frequency to the Nyquist frequency, respectively in the perpendicular two periodicity directions of the pixel arrangement of the X-ray detector. By doing so, since the maximum frequency region centering on the carrier peak is cut out, the spatial resolution of the calculated differential phase distribution is maximized.

Example 4

As an example 4, a constructive example of the X-ray imaging apparatus which is different from those in the above examples 1 to 3 will be described with reference to FIGS. 11A to 11H and FIG. 12.

In this example, only portions which are different from the examples 1 to 3 will be described. Incidentally, although the diffraction grating which has periodicity in the two directions is used as the diffraction grating in the examples 1 to 3, the phase modulation grating or the intensity modulation grating which has periodicity in one direction is used in this example.

The diffraction grating having periodicity in one direction has an advantage that manufacturing is easier than the diffraction grating having periodicity in two directions.

FIGS. 11A, 11B and 11C respectively illustrate the position state of the diffraction grating, the intensity distribution on the X-ray detector, and the frequency spectrum obtained by performing the two-dimensional Fourier transform to the intensity distribution on the X-ray detector, in a case where the phase modulation grating which periodically modifies the phase in one direction by $\pi/2$ is used.

FIGS. 11D, 11E and 11F respectively illustrate the position state of the diffraction grating, the intensity distribution on the X-ray detector, and the frequency spectrum obtained by performing the two-dimensional Fourier transform to the intensity distribution on the X-ray detector, after the diffraction grating was moved so as to deviate the intensity distribution on the X-ray detector in the horizontal direction having periodicity by a half period.

FIG. 11G illustrates the difference between the intensity distributions before and after the movement of the diffraction grating, and FIG. 11H illustrates the difference between the frequency spectra before and after the movement of the diffraction grating.

As illustrated in FIG. 11H, since unnecessary peaks other than the carrier peak have been eliminated, a difference in the differential phase distribution is recued.

Here, the differential phase distribution is calculated from the difference spectrum illustrated in FIG. 11H according to the steps 160, 170 and 180.

When the period of the intensity distribution is four times the size of the pixel of the X-ray detector and the periodicity direction of the intensity distribution coincides with the arrangement direction of the pixels of the X-ray detector, the spatial resolution of the differential phase distribution to be calculated is maximized.

Figure 12:
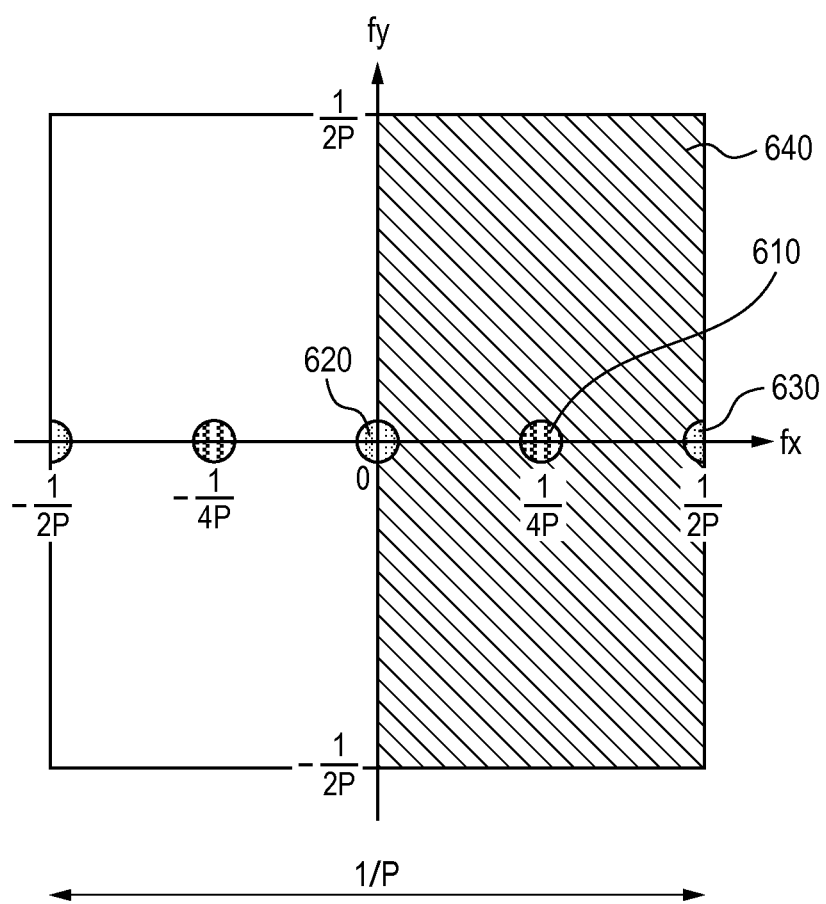
FIG. 12 is a diagram for describing a frequency spectrum cut-out region in the example 4 of the present invention.

FIG. 12 illustrates the frequency spectrum at this time. As illustrated in the drawing, a peak 620 at the center and a peak 630 corresponding to a second harmonic of the carrier peak have been eliminated by the difference of the imaging intensity distribution obtained after the movement of the diffraction grating. Thus, a region 640 which is a hatched-line rectangular region and based on a carrier peak 610 can be cut out.

This region, that is, the frequency region which includes frequencies from a zero frequency to a Nyquist frequency in the periodicity direction of the intensity distribution and includes the overall frequency region between the Nyquist frequencies in the direction perpendicular to the periodicity direction of the intensity distribution is maximum as the region to be cut out as centering on the carrier peak. Thus, the spatial resolution of the calculated differential phase distribution is maximized.

Even in the case where the phase modulation grating of the phase difference $\pi$ or the phase modulation grating is used, the differential phase distribution in which the error has been reduced can be calculated based on the two imaging intensity distributions obtained by moving the diffraction grating so as to deviate the intensity distribution by a half period, as well as the phase modulation grating of the phase difference $\pi/2$.

When the phase modulation grating of the phase difference $\pi/2$ is used, the movement amount of the diffraction grating is $\frac{1}{2}$ of the grating period. When the phase modulation grating of the phase difference $\pi$ is used, the movement amount of the diffraction grating is $\frac{1}{4}$ of the grating period. When the intensity modulation grating is used, the movement amount of the diffraction grating is $\frac{1}{2}$ of the grating period.

In this example, the phase distribution can be obtained by integrating the obtained differential phase of the diffraction grating in the periodicity direction.

To more accurately calculate the phase distribution, for example, it is possible to calculate the differential phases in the two or more directions by changing the periodicity direction by rotating the diffraction grating within the plane, and obtain the phase distribution by which the calculated differential phases are simultaneously satisfied.

Example 5

Figure 13:
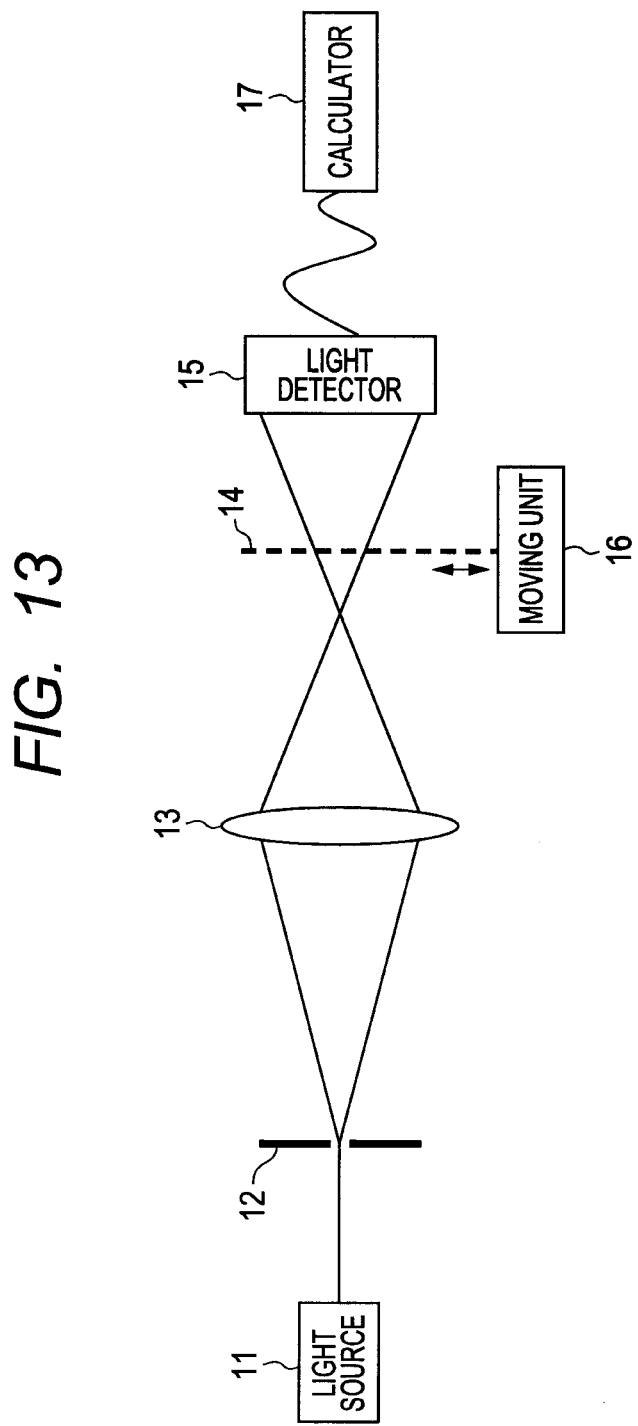
FIG. 13 is a block diagram for describing a constructive example of a wavefront measuring apparatus according to an example 5 of the present invention.

As an example 5, a constructive example of the wavefront measuring apparatus will be described with reference to FIG. 13.

In this example, only portions which are different from the examples 1 to 4 will be described.

A light source 11, which is constituted by, e.g., a laser, radiates coherent light. A specimen 13 is, e.g., an optical element, and more concretely a lens or a lens group which is a target of wavefront measurement.

An illumination optical system 12, which is disposed between the light source 11 and the specimen 13, converts a light wave generated by the light source 11 into a wavefront of which the aberration has been known. The illumination optical system 12 is constituted by, e.g., a pinhole of which the aperture is sufficiently small, and generates the wavefront which is approximated by a spherical wave.

A diffraction grating 14 periodically modulates an intensity or a phase of the light radiated by the light source, in one direction or perpendicular two directions. The light which transmitted through the diffraction grating 14 generates a periodic intensity distribution by the Talbot effect, at a position which satisfies the above-described expression (1).

A light detector 15 is a two-dimensional imaging element which images the intensity distribution. A CCD or the like is used as the light detector 15. A moving unit 16, which moves the diffraction grating 14 in a plane, can move the intensity distribution in the periodicity direction by a half period. A calculator 17 calculates a differential phase distribution of incident light to the diffraction grating 14, from the imaging intensity distribution obtained according to the procedure indicated in FIG. 3. Namely, it is possible, from the differential phase distributions in the perpendicular two directions, to obtain the phase distribution which simultaneously satisfies these distributions, that is, the transmitted wavefront of the specimen 13.

As just described, the embodiments and the examples of the present invention are explained. However, the present invention is not limited to these embodiments and examples. Namely, various modifications and equivalent arrangements can be attained within the spirit and scope of the invention.

The technical components described in the specification or the drawings exert technical utility by themselves or by various combinations thereof, but are not limited to the combination described in the appended claims. Further, the technique exemplified in the specification or the drawings accomplishes plural objects simultaneously. Furthermore, the technique has technical utility by accomplishing one of these objects.

Industrial Applicability

The present invention can be used to an X-ray imaging apparatus which measures an X-ray phase image of a specimen, and a wavefront measuring apparatus which measures a transmitted wavefront of the specimen.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-016606, filed Jan. 28, 2010, which is hereby incorporated by reference herein in its entirety.

REFERENCE SIGNS LIST

1 X-ray source
2 X-ray
3 specimen
4 diffraction grating
5 X-ray detector
6 diffraction grating moving unit
7 calculator

The invention claimed is:

1. An X-ray imaging apparatus which images a specimen, comprising:
an X-ray source;
a diffraction grating configured to diffract X-rays from said X-ray source;
an X-ray detector configured to detect the X-rays diffracted by said diffraction grating; and
a calculator configured to calculate phase information of the specimen on the basis of an intensity distribution of the X-rays detected by said X-ray detector,
wherein said X-ray detector detects a first intensity distribution and a second intensity distribution different from the first intensity distribution by a half period, and
said calculator obtains a spatial frequency spectrum of a difference between the first intensity distribution and the second intensity distribution, and calculates the phase information from the obtained spatial frequency spectrum.

2. The X-ray imaging apparatus according to claim 1, further comprising a moving mechanism configured to move the diffraction grating,
wherein said moving mechanism moves said diffraction grating so that the intensity distribution is moved by a half period, and
the plural intensity distributions include the intensity distribution before the movement by said moving mechanism and the intensity distribution after the movement by said moving mechanism.

3. The X-ray imaging apparatus according to claim 2, wherein
said diffraction grating is constituted to periodically modify a phase or an intensity of the X-rays in one direction, and
said moving mechanism moves said diffraction grating so that the intensity distribution is moved by the half period in the one direction.

4. The X-ray imaging apparatus according to claim 3, wherein
a period of the intensity distribution is four times a size of a pixel of said X-ray detector,
a periodicity direction of the intensity distribution coincides with an arrangement direction of the pixels of said X-ray detector, and
said calculator cuts out, from the spatial frequency spectrum, a rectangular region which includes frequencies from a zero frequency to a Nyquist frequency in the periodicity direction of the intensity distribution and includes a frequency between the Nyquist frequencies in a direction perpendicular to the periodicity direction of the intensity distribution.

5. The X-ray imaging apparatus according to claim 3, wherein
said diffraction grating is constituted to periodically modify a phase or an intensity of the X-rays in two directions mutually perpendicular to each other, and
said moving mechanism moves said diffraction grating so that the intensity distribution is moved by the half period in the two directions.

6. The X-ray imaging apparatus according to claim 5, wherein
a period of the intensity distribution is $2\sqrt{2}$ times a size of a pixel of said X-ray detector,
a periodicity direction of the intensity distribution is inclined in regard to an arrangement direction of the pixels of said X-ray detector by 45°, and
said calculator cuts out, from the spatial frequency spectrum, a square region which includes frequencies from a zero frequency to a Nyquist frequency.

7. The X-ray imaging apparatus according to claim 1, further comprising a shielding member which is disposed between said diffraction grating and said X-ray detector,
wherein said shielding member generates a moiré fringe by shielding a part of the X-rays diffracted by said diffraction grating,
said X-ray detector detects the moiré fringe as the intensity distribution, and
said calculator calculates the phase information on the basis of the generated moiré fringe.

8. The X-ray imaging apparatus according to claim 7, further comprising a moving mechanism configured to move said shielding member,
wherein said moving mechanism moves said shielding member so that the intensity distribution is moved by a half period, and
the plural intensity distributions include the intensity distribution before the movement by said moving mechanism and the intensity distribution after the movement by said moving mechanism.

9. The X-ray imaging apparatus according to claim 1, wherein said calculator obtains the spatial frequency spectrum of the difference by performing a Fourier transform on a difference image between the first intensity distribution and the second intensity distribution.

10. The X-ray imaging apparatus according to claim 1, wherein said calculator calculates a frequency spectrum of the first intensity distribution and a frequency spectrum of the second intensity distribution by performing a Fourier transform respectively on the first intensity distribution and the second intensity distribution, and said calculator obtains the spatial frequency spectrum of the difference by calculating a difference between the frequency spectrum of the first intensity distribution and the frequency spectrum of the second intensity distribution.

11. The X-ray imaging apparatus according to claim 1, wherein said calculator separates a frequency component in a period of the intensity distribution from the spatial frequency spectrum of the difference, and said calculator calculates the phase information from the spatial frequency spectrum of the difference by using the separated frequency component.

12. The X-ray imaging apparatus according to claim 11, wherein said calculator separates the frequency component by cutting out, from the spatial frequency spectrum of the difference, an inner side of a peak of the frequency component in the period of the intensity distribution from an intermediate line between the peak of the frequency component in the period of the intensity distribution and another peak.

13. The X-ray imaging apparatus according to claim 11, wherein said calculator calculates the phase information by performing an inverse Fourier transform on a peak of the frequency component separated from the spatial frequency spectrum of the difference.

14. The An X-ray imaging apparatus which images a specimen, comprising:

an X-ray source;

a diffraction grating configured to diffract an X-ray from the X-ray source;

an X-ray detector configured to detect the X-ray diffracted by the diffraction grating; and a calculator configured to calculate phase information of the specimen on the basis of an intensity distribution of the X-ray detected by the X-ray detector, wherein said X-ray detector detects an intensity distribution IA, an intensity distribution IB obtained by moving the intensity distribution IA in a first direction, an intensity distribution IC obtained by moving the intensity distribution IA in a second direction perpendicular to the first direction, and an intensity distribution ID obtained by moving the intensity distribution IA in the first direction and the second direction, and said calculator obtains the a spatial frequency spectrum of an intensity distribution IE which satisfies an expression IE=IA−IB−IC+ID, and calculates the phase information from the obtained spatial frequency spectrum.

* * * * *